United States Patent [19]

Shimazaki et al.

[11] 4,013,800
[45] Mar. 22, 1977

[54] 4-HYDROXY-5-METHYL-2,3-DIHYDROFURAN-3-ONE AND METHODS OF MAKING AND USING THE SAME

[75] Inventors: Hideo Shimazaki, Tokyo; Shuji Tsukamoto; Tadaomi Saito, both of Yokohama; Sadanari Eguchi, Sendai; Yasushi Komata, Tokyo, all of Japan

[73] Assignee: Ajinomoto Co., Inc., Tokyo, Japan

[22] Filed: July 16, 1971

[21] Appl. No.: 163,434

Related U.S. Application Data

[60] Division of Ser. No. 881,951, Dec. 29, 1969, Pat. No. 3,647,825, which is a continuation-in-part of Ser. No. 712,397, March 12, 1968, abandoned.

[30] Foreign Application Priority Data

Mar. 15, 1967 Japan ............... 42-16265
Apr. 15, 1967 Japan ............... 42-23921

[52] U.S. Cl. ............................. 426/536
[51] Int. Cl.$^2$ ................ A23L 1/22; A23L 1/231
[58] Field of Search ........... 99/140 R; 260/347.8; 426/536

[56] References Cited

UNITED STATES PATENTS 3,455,702  7/1969  Willhalm et al. ............ 99/140 R
3,697,291  10/1972  Tonsbeek .................... 99/140 R

OTHER PUBLICATIONS

Hodge, et al. "Dicarbonyls, Reductones, and Heterocyclics Produced by Reactions of Reducing Sugars with Secondary Amine Salts," *American Society of Brewing Chemists Proceedings*–Annual Meeting–(1963) pp. 84–92.

Rodin et al., "Volatile Flavor and Aroma Components of Pineapple," *J. Food Science*, vol. 30, (1965) pp. 280–285.

*Primary Examiner*—Morris O. Wolk
*Assistant Examiner*—Sidney Marantz

[57] ABSTRACT

4-Hydroxy-5-methyl-2,3-Dihydrofuran-3-one is produced by Maillard reaction between xylose, ribose or arabinose with glutamic acid, aspartic acid, alanine, glycine, proline or salts of these amino acids, and may be recovered in crystalline form from the reaction mixture by steam distillation, evaporation of the distillate at temperatures not higher than 40° C, and sublimation from the oily residue at or above 80° C. The compound imparts a pleasant maltol-like flavor to ingestible products such as food, drinks, but also compositions for oral hygiene. The crude Maillard reaction mixture containing the compound may be employed as a flavoring if prepared from glutamic acid, aspartic acid or their salts and from xylose or xylan.

13 Claims, No Drawings

4-HYDROXY-5-METHYL-2,3-DIHYDROFURAN-3-ONE AND METHODS OF MAKING AND USING THE SAME

This application is a division of the copending application Ser. No. 888,951, filed Dec. 29, 1969, now U.S. Pat. No. 3,647,825, which itself is a continuation-in-part of the application Ser. No. 712,397, filed on Mar. 12, 1968, and now abandoned.

This invention relates to improvements in the flavor and aroma of ingestible compositions such as food, drink, oral hygiene compositions and the like not normally intended to be swallowed, but ingestible and normally acting on the senses of taste and smell.

Maltol has been used as a flavoring agent to impart the characteristic "freshly baked" odor to bread and cakes. It has now been found that the products of a Maillard reaction between certain amino acids and pentoses are capable of imparting a maltol-like flavor to food and of improving the flavor and aroma of food and other ingestible compositions where the improvement does not necessarily involve the characteristic maltol effect.

We have identified the primary flavoring agent in the Maillard reaction mixture as 4-hydroxy-5-methyl-2,3-dihydrofuran-3-one and have isolated the compound from the reaction mixture. The crude mixture may be employed as a flavoring agent when prepared from glutamic acid or aspartic acid or their non-toxic salts and from xylose or xylane which yields xylose under the conditions of the Maillard reaction in an aqueous medium.

The non-toxic salts preferably employed when the free amino acids are unavailable are the alkali metal, alkaline earth metal and ammonium salts of the amino acids, but it will readily be apparent that the nature of the cationic moiety of the salt is irrelevant as long as it does not render the ultimate product toxic.

A crude Maillard reaction mixture suitable as a flavoring agent may be prepared by heating glutamic acid or aspartic acid and 0.5 to 50 mol xylose per mol amino acid in a liquid medium to a temperature between about 60° and 180° C. Water is the preferred solvent, and the aqueous solution should be adjusted to pH 7 to 10.5 and held at 85° to 100° C until it becomes yellow or reddish yellow, which usually requires 20 to 30 minutes. When the solvent is removed and the residue is converted to a powder, it may be added to solid or liquid food or to oral hygiene compositions in an amount of 0.05 to 10% by weight, the exact dosage depending on the nature of the ingestible composition and on the desired result.

Xylan hydrolyzes to xylose under the conditions of the Maillard reaction in an aqueous medium, and may be substituted for xylose in equivalent amounts or equal weights. When the ingestible composition is prepared by heating under conditions suitable for the Maillard reaction, the amino acid and the xylose or xylane may be added to the raw material, and the Maillard reaction performed during cooking, baking or other heat treatment of the raw material.

The principal flavoring component of the Maillard reaction product is 4-hydroxy-5-methyl-2,3-dihydrofuran-3-one which has been prepared in pure crystalline form as will be described hereinbelow.

The compound in the pure form or as a crude mixture has been added with beneficial results to bread, biscuits, candy, chocolate, meat and processed meat, milk products, processed food prepared from eggs, fresh and smoked fish and vegetables, also to powdered soup concentrates, dried fruits and nuts, canned fruits, soft drinks, liqueur, wine, whiskey, instant coffee, but also cigars and cigarettes, chewing gum and oral hygiene preparations such as toothpastes, mouthwashes and mouthwash concentrates.

The following Examples further illustrate the invention:

EXAMPLE 1

A solution of 20 g monosodium L-glutamate and 20 g xylose in 200 ml water was adjusted to pH 9.5 with sodium hydroxide. The alkaline solution was held at 85° C for 20 minutes. It was then adjusted to pH 6.4 and evaporated to dryness in a vacuum. The residue was a light yellow powder weighing 40 g and having a pleasant smell like that of maltol.

100 g Powdered cheese were mixed with 0.5 g of the powder obtained from the above Maillard reaction between the glutamate and the xylose. Samples of the cheese powder with and without the Maillard reaction product were submitted for an organoleptic test to a panel of 30 members well trained in such tests. 25 Panelists preferred the cheese containing the Maillard reaction product, and the other 5 did not notice a difference.

Ice cream was prepared in a conventional manner with refined soybean protein powder which contained 0.1% (by weight) of the Maillard reaction product. A control batch of ice cream was prepared in the same manner but without the Maillard reaction product. Of a panel of 35 trained tasters, 30 members preferred the ice cream prepared with the Maillard reaction product, and 24 of the 30 noticed a substantial improvement in the suppression of the soybean aroma and in added maltol-like flavor.

EXAMPLE 2

A solution of 20 g monosodium L-glutamate, 10 g aspartic acid and 30 g xylose in 300 ml water was adjusted to pH 9.5 and kept at 85° C for 30 minutes, whereby its color changed to a reddish brown. The pH was then adjusted to 6.5, and the solution was evaporated to dryness in a vacuum to yield 60 g of a Maillard reaction product which was a yellowish-brown powder and had a flavor and aroma similar to maltol.

A panel of 35 tasters was presented with soy sauce containing 1% (by weight) of the powder and with a control sample without the powder. 29 Tasters preferred the sauce containing the powder for its aroma and flavor whereas the other six could not find any significant difference.

EXAMPLE 3

Two batches of biscuits were baked at 180° C from the same conventional dough, but 0.5% monosodium glutamate and 0.5% xylose (by weight) were mixed with the dough for one batch prior to baking at 180° C. In a panel of 40 tasters, 36 preferred the flavor and aroma of the biscuits made with added glutamate and xylose. 31 Tasters indicated a substantial improvement in aroma.

EXAMPLE 4

500 g Monosodium L-glutamate and 500 g xylose were suspended in 500 ml water, live steam was passed through the suspension for 2 hours and 2 liters of distillate were collected by condensation. When the distillate was evaporated in a vacuum at a temperature not higher than 40° C, 5 g of an oily material were obtained. The oily material was kept at 80° C in a vacuum of 10 mm Hg, whereby a crystalline sublimate was deposited on the walls of the container in an amount of 100 mg.

The crystals which were colorless and needle-shaped had a strong aroma similar to that of maltol and a melting point of 126°–127° C. They were identified as 4-hydroxy-5-methyl-2,3-dihydrofuran-3-one of the formula

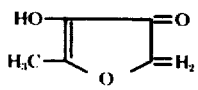

in good agreement with the closely similar results of two elementary analyses:

| 53.20% C; | 5.48% H; | 41.32% O |
|---|---|---|
| 53.33 | 5.45 | 41.22 |

When ferric chloride reagent was added to an aqueous solution of the crystals, the solution turned bluish black. A solution acidified with sulfuric acid did not show a reaction with 2,4-dinitrophenylhydrazine. A pink color developed in the pine splinter test. The aqueous solution showed maximum absorption for ultraviolet light at 283–286 mu.

The infrared absorption spectrum of the compound has a broad maximum value ($\int$ KBr) at 3,200 cm$^{-1}$ indicative of a hydroxyl group, a relatively sharp maximum at 1690–1695 cm$^{-1}$ indicative of a carbonyl group, and another relatively sharp maximum at 1,630–1,640 cm$^{-1}$, indicative of a double bond.

The nuclear magnetic resonance spectrum was determined at 60 MC in chloroform solution against a tetramethylsilane standard. It contained characteristic peaks at 2.28 ppm indicative of hydrogen ion in the methyl group of a cyclic compound, at 4.5 ppm indicative of hydrogen ion in a methylene group of a cyclic compound, and at 7.23 ppm indicative of hydrogen ion in a hydroxyl group of a cyclic compound.

A solution of 4-hydroxy-5-methyl-2,3-dihydrofuran-3-one in water or pure ethanol at a concentration of 10 ppm to 500 ppm had a flavor and aroma more refined and sweeter than that of maltol.

The same compound was obtained when the glutamate in the above procedure was replaced by optically active or inactive glutamic acid, aspartic acid, alanine, glycine, proline, or by alkali metal, ammonium, or alkaline earth salts of these acids. Similarly, the xylose could be replaced by arabinose or ribose, and the mol ratio of the pentose to the amino acid in the reaction mixture could be varied from 1:2 to 50:1. The same compound was also obtained by heating a dry mixture of the amino acid and of the pentose in the form of powders, and by a work-up of the reaction mixture by sublimation in a vacuum of 5 to 20 mm Hg at a temperature above 80° C. The first described steam distillation method, however, is preferred.

EXAMPLE 5

A 1% aqueous solution of 4-hydroxy-5-methyl-2,3-dihydrofuran-3-one was added to a portion of a chocolate cake mix in an amount of 120 ppm based on the weight of the flavoring compound and of chocolate in the mix. Chocolate cakes were prepared from both portions of the batch.

When samples of the two types of cakes were submitted to a panel of 40 tasters, 32 panel members indicated a preference for the chocolate cake containing 4-hydroxy-5-methyl-2,3-dihydrofuran-3-one because of better flavor and aroma whereas the other eight did not find a significant difference.

EXAMPLE 6

200 Parts per million (by weight) 4-hydroxy-5-methyl-2,3-dihydrofuran-3-one as a 1% aqueous solution were added to a commercial dry mix for hot cakes, and cakes were prepared from the modified mix, and from the same mix without the added solution.

In an organoleptic test, all 20 members of a panel of experts preferred the flavor and aroma of the cakes prepared with 4-hydroxy-5-methyl-2,3-dihydrofuran-one.

EXAMPLE 7

Of two batches of commercial pineapple juice, one was mixed with 25 ppm of the 1% solution described in the preceding Examples, and the two batches were submitted to a panel of 25 tasters for an organoleptic test. 23 Panelists preferred the juice containing a minute amount of 4-hydroxy-5-methyl-2,3-dihydrofuran-3-one.

EXAMPLE 8

Four drops of the 1% solution were added to 720 ml sherry, and the prepared sherry was submitted to a panel of 30 members for comparison with the same sherry not mixed with 4-hydroxy-5-methyl-2,3-dihydrofuran-3-one. 25 Tasters considered the prepared sherry mellower than the untreated sherry.

EXAMPLE 9

One-half of a batch of commercial, smoked pork sausages was sprayed with the aforementioned 1% solution before the sausages were submitted to a panel of 25 tasters for an organoleptic test.

19 Panelists preferred the smoke flavor of the treated sausages, whereas the other 6 could not find a significant difference.

EXAMPLE 10

Two drops of the 1% solution were added to 100 ml of a mouthwash prepared from a commercial product containing palmitoyl-L-valine as a germicide. The aroma and taste of the mouthwash were substantially improved.

EXAMPLE 11

Enough of the 1% solution were added to one-half of a batch of beef consomme to make the concentration of 4-hydroxy-5-methyl-2,3-dihydrofuran-3-one 25 ppm.

When the two types of soup were submitted to a panel of 25 tasters, the soup containing the addition agent was preferred by 18 members of the panel.

Xylose has been replaced successfully by xylan in the Maillard reactions of the invention in equivalent amounts, that is, in amounts to yield the desired xylose when the xylan is hydrolyzed under the conditions of the Maillard reaction. The xylan may be derived at low cost from peanut shells or similar vegetal wastes, and is commercially available.

What is claimed is:

1. A method of imparting a maltol-like flavor and aroma to an ingestible composition which comprises mixing said composition with 10 to 500 parts per million (by weight) of 4-hydroxy-5methyl-2,3-dihydrofuran-3-one, based on the weight of said ingestible composition.

2. A method as set forth in claim 1, wherein said ingestible composition is baked after said mixing thereof with said 4-hydroxy-5-methyl-2,3-dihydrofuran-3-one.

3. A method as set forth in claim 1, wherein said ingestible composition is a cheese.

4. A method as set forth in claim 1, wherein said 4-hydroxy-5-methyl-2,3-dihydrofuran-3-one is in the crystalline state prior to said mixing thereof with said ingestible composition.

5. A method as set forth in claim 4, wherein said crystalline 4-hydroxy-5-methyl-2,3-dihydrofuran-3-one is dissolved in water prior to said mixing, and the resulting aqueous solution is mixed with said ingestible composition.

6. A method as set forth in claim 1, wherein said ingestible composition is a meat product.

7. A method as set forth in claim 6, wherein said meat product is a sausage or a soup.

8. A foodstuff consisting essentially of a meat product or a meat simulating product and a 4-hydroxy-2,3-dihydrofuran-3-one of the formula

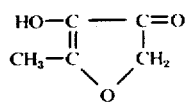

9. A foodstuff as claimed in claim 8 in which the quantity of the furanone present, calculated on the weight of ready-for-use foodstuff, is from 10 to 500 parts per million.

10. A foodstuff as claimed in claim 8 in which the 4-hydroxy-2,3-dihydrofuran-3-one is added to the foodstuff in the form of a precursor.

11. A foodstuff in accordance with claim 8, wherein said foodstuff is a soup.

12. A method of flavoring a meat product or simulated meat product, comprising introducing an effective flavoring amount of a meat flavor composition consisting essentially of a 4-hydroxy-2,3-dihydrofuran-3-one of the formula

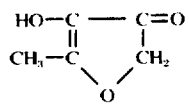

into the meat product or simulated product.

13. A method in accordance with claim 12, in which the amount of furanone added is from 10 to 500 parts per million by weight, based on the weight of the meat product or simulated meat product.

* * * * *